United States Patent [19]

Moore, Jr. et al.

[11] Patent Number: 5,150,621
[45] Date of Patent: Sep. 29, 1992

[54] APPARATUS FOR COLLECTING SAMPLES OF ARTICLES CONVEYED AT HIGH SPEED IN CONSECUTIVE ORDER

[75] Inventors: Jack S. Moore, Jr., Blountville; Johnny R. Cox; Mark L. Williams, both of Kingsport, all of Tenn.

[73] Assignee: Eastman Kodak Company, Rochester, N.Y.

[21] Appl. No.: 607,967

[22] Filed: Nov. 1, 1990

[51] Int. Cl.⁵ .............................................. G01N 1/00
[52] U.S. Cl. .................................................. 73/863.91
[58] Field of Search ............... 73/863, 863.41, 863.91, 73/863.92, 864, 864.31; 198/690.1, 689.1, 688.1; 131/905, 908–910

[56] References Cited

U.S. PATENT DOCUMENTS

| | | | |
|---|---|---|---|
| 3,320,110 | 5/1967 | Gallagher | 156/438 |
| 3,881,356 | 5/1975 | Palm | 73/863.91 |
| 4,586,601 | 5/1986 | Hodlewsky | 198/690.1 |
| 4,593,805 | 1/1986 | Huddle | 198/690.1 |
| 4,962,771 | 10/1990 | Neri et al. | 73/863.91 |

FOREIGN PATENT DOCUMENTS 3322428 1/1985 Fed. Rep. of Germany ... 198/688.1

*Primary Examiner*—Robert Raevis
*Attorney, Agent, or Firm*—John F. Stevens; William P. Heath, Jr.

[57] ABSTRACT

This invention relates to apparatus for collecting consecutive samples of articles from a production line which are being conveyed at a high rate of speed. Samples are collected from the production line by transferring them to a conveyor which carries them to storage in sequential order. The invention is particularly applicable to collecting cigarette filter rods or cigarettes in the order of their production for subsequent testing and/or analysis.

6 Claims, 4 Drawing Sheets

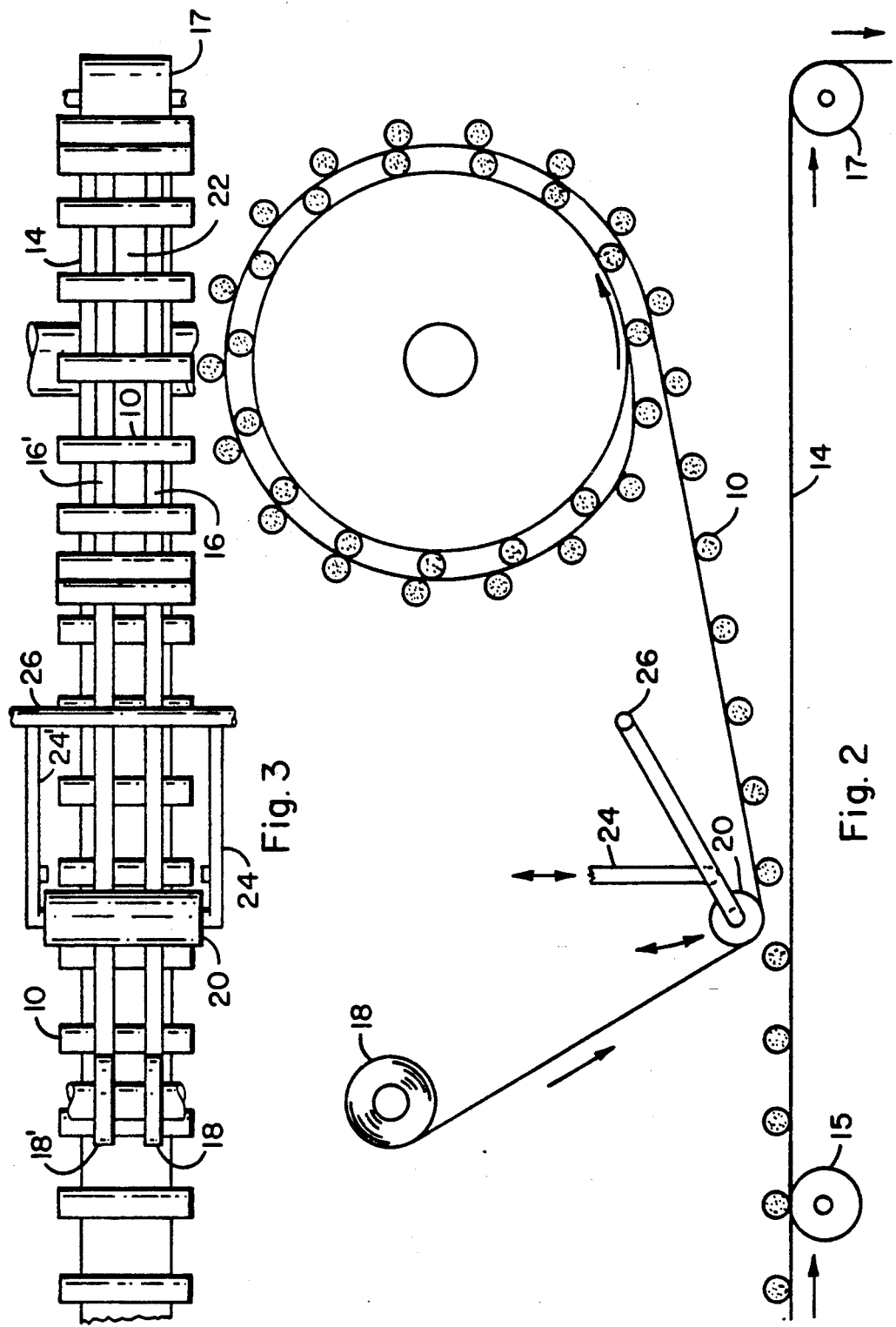

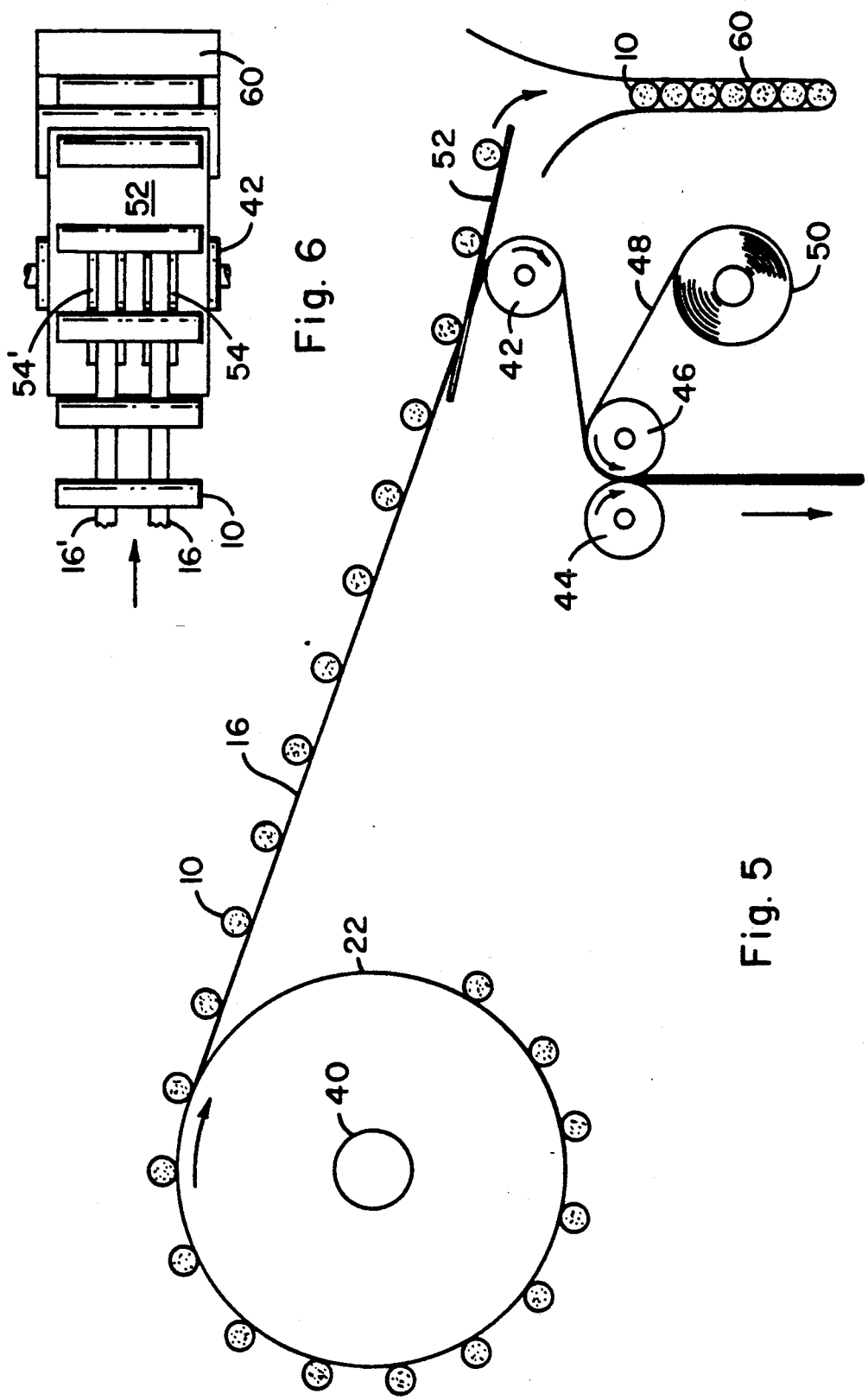

APPARATUS FOR COLLECTING SAMPLES OF ARTICLES CONVEYED AT HIGH SPEED IN CONSECUTIVE ORDER

TECHNICAL FIELD

This invention relates to apparatus for collecting consecutive samples of articles from a production line which are being conveyed at a high rate of speed. The invention is particularly applicable to collecting cigarette filter rods or cigarettes in the order of their production for subsequent testing and/or analysis.

BACKGROUND OF THE INVENTION

This invention is applicable in general to the collection of articles from a production line moving at high speed in the order of their production. The invention will be described herein with particular reference to collecting elongated, light weight cigarette filter rods in the order of their production for test purposes. The invention should find application in instances where articles having a surface which can be attached to by a strip of material such as adhesive tape are being conveyed.

To properly determine how filter rod properties and quality change as the operating conditions change on production equipment (commonly called plugmaker), the rods must be individually analyzed in the order in which they were produced. A problem has existed, however, in that the rods are produced and conveyed away from the production equipment at such high speeds that it is very difficult to collect samples in consecutive order for testing and/or analysis. In the past, when one wanted to collect rods for analyses, a number of people were assembled and each person used boards which had masking tape attached to them with the "sticky" side turned down. The boards would be pressed down on the rods as exit the plugmaker. This technique was unsatisfactory; some rods were missed, some were damaged or crushed during the collecting step, some were damaged when they were pulled from the masking tape for testing and it was very labor intensive. Therefore, there exists a need for apparatus for taking samples from a high speed conveyor in the order in which they were made for subsequent testing and/or analysis.

BRIEF DESCRIPTION OF THE DRAWINGS

FIG. 2 is an elevation view of the apparatus according to the present invention picking up articles to be analyzed;

FIG. 3 is a plan view of the apparatus shown in FIG. 2;

FIG. 5 is an elevation view of apparatus for removing articles from the apparatus shown in FIGS. 2-4; and FIG. 6 is a partial plan view of the apparatus shown in FIG. 5.

DESCRIPTION OF THE INVENTION

According to the present invention, there is provided an apparatus for intermittently sampling articles comprising (a) a first conveyor for advancing articles along a predetermined path,
(b) a second conveyor having means for attaching to the articles and adapted to be advanced along a path adjacent to and generally co-directional with the articles, said second conveyor having a first position spaced from said articles and a second position contacting said articles,
(c) means for advancing said second conveyor along said path at approximately the same speed as the articles on said first conveyor,
(d) means for moving said second conveyor from said first position to said second position, whereby said articles are transferred from said first conveyor to said second conveyor.

Figure 1:
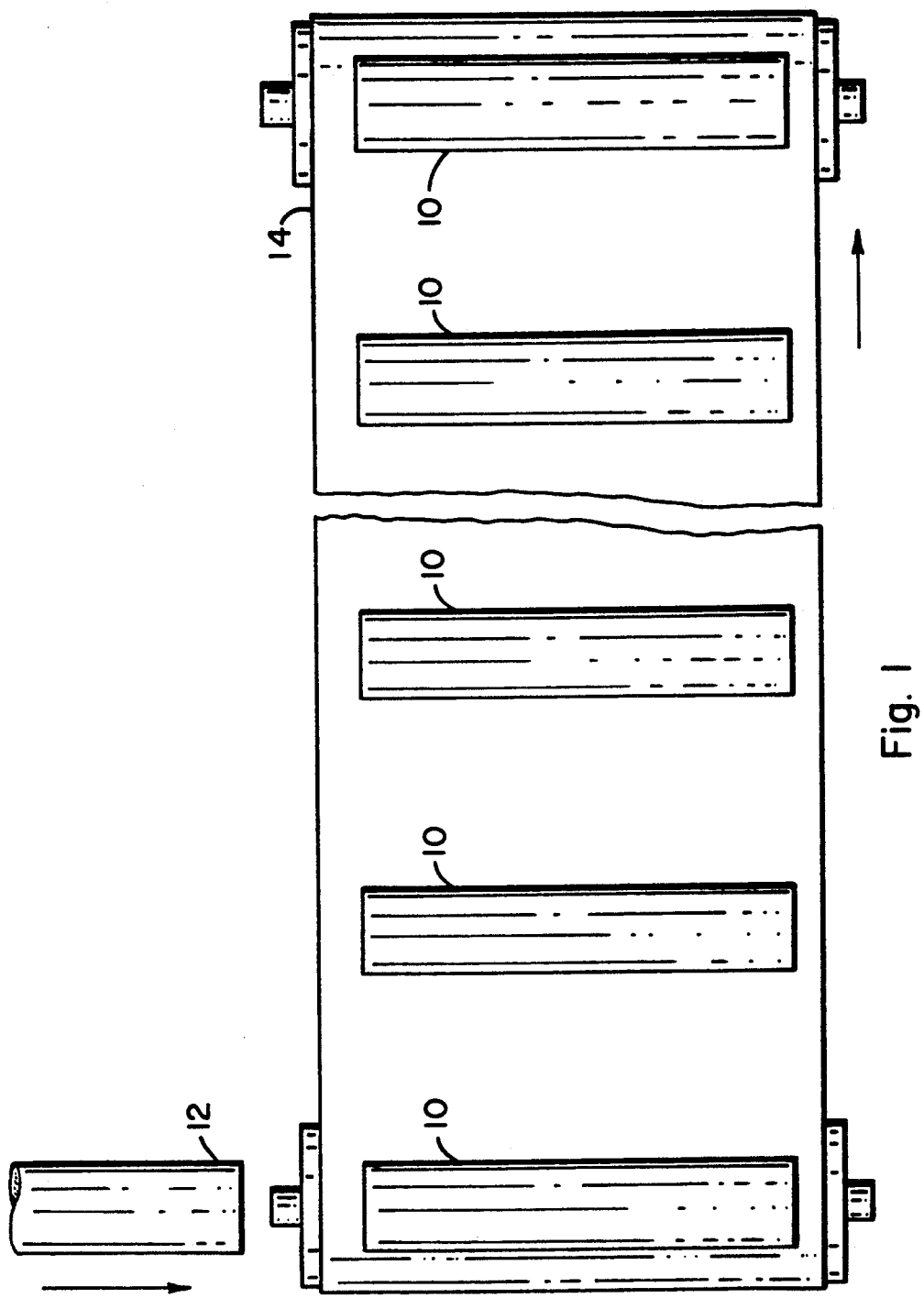
FIG. 1 is a schematic plan view of articles to be sampled being advanced in side-by-side relationship.

Cigarette filter rods are conventionally made in the form of a continuous rod and subsequently cut into lengths of about 3-5 inches. Normally, they emerge from the rod making machine in parallel, side-by-side alignment in the order in which they are cut. As illustrated in FIG. 1, individual fibrous rods 10 are successively cut from the advancing continuous length of rod 12. Suitable means for forming the continuous rod and cutting means are well known in the art. See, for example, U.S. Pat. No. 3,320,110. As the individual rods are cut, they are positioned in generally parallel, side-by-side alignment on a first conveyor belt 14 which is advancing in the direction of the arrow. The individual rods are formed at a high rate, for example, about 50 per second. Normally, the rods 10 would be directed to a container where they would be randomly deposited.

The invention is best illustrated in FIGS. 2-6. The articles to be sampled 10 are illustrated in side-by-side position on a first conveyor 14 supported on rollers 15 and 17. Articles 10 in this case are lightweight, cylindrical, elongated cigarette filter rods as described above. The articles 10 are positioned on first conveyor 14 in consecutive order in which they were produced. The articles 10 are advanced by conveyor 14 along a predetermined path, in this case a horizontal run, as determined by the positioning of convey 14. Normally, articles 10 would drop off the end of first conveyor 14 into a receptacle (not shown).

Figure 4:
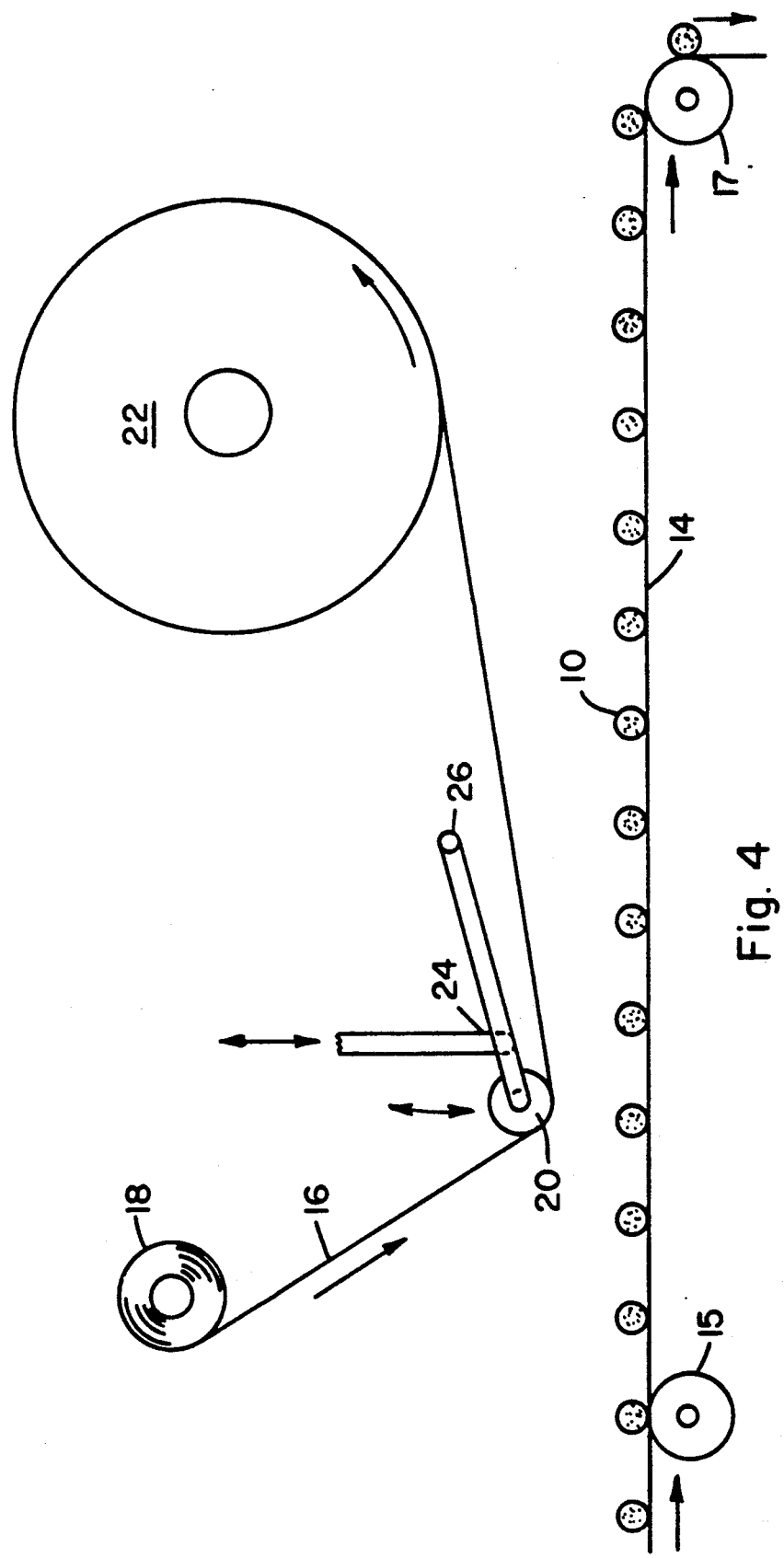
FIG. 4 is an elevation view of the apparatus shown in FIG. 2 at rest.

A second conveyor 16, 16' is positioned such as to have at least a portion of its path adjacent to and generally co-directional with articles 10. Second conveyor 16, 16' has a first position spaced from articles 10 as illustrated in FIG. 4, and a second position for contacting articles 10 as illustrated in FIG. 2. Second conveyor 16, 16' in this case is a pair of spaced apart adhesive tapes supplied from rolls 18, 18'. The tapes have their adhesive-coated side turned out from the center of the supply rolls. Tapes 16, 16' are directed around idler roll 20, and the ends thereof are attached to a driven take-up drum 22. The adhesive coating on tapes 16, 16' may be used for attaching the ends thereof to roll 22. Idler roll 20 is rotatably mounted on a pair of arms 24, 24', which are pivoted about point 26. The position of Arms 24, 24' may be changed from those shown in FIGS. 2 and 4 by any convenient means such as, for example, pneumatic cylinder(s) or solenoid(s).

The second conveyor has been illustrated as a pair of tapes having adhesive coatings on one side. Obviously, however, the second conveyor may be in other forms depending on the articles being handled. For example, the articles may be metallic strips in which case the second conveyor may contain magnetic material. Other materials for the second conveyor will be obvious to those skilled in the art depending on the articles 10.

Means are provided for rotating the drum 22 in the direction shown by the arrow at a speed so as to advance tapes 16, 16' at approximately the same speed as the rods 10 are being moved on conveyor 14.

In operation, arms 24, 24' are normally in the first position shown in FIG. 4, and the drum 22 is stationary. Thus, the second conveyor and idler roll 20 are stationary. Articles 10 are being advanced at a high rate of speed by conveyor 14 and are allowed to drop into a container (not shown).

When it is desired to take a sample of articles, the free ends of tape 16, 16' are guided around roll 20 and adhered to the surface of drum 22. The adhesive coating on tape 16 is next to articles 10. Drum 22 is rotated as described above, usually for several revolutions. Simultaneously as the drum 22 begins to rotate, arms 24, 24' are pivoted about point 26 to the second position as shown in FIG. 2. As the tape contacts the articles 10 with its adhesive coating, articles 10 will adhere thereto and be wound with tape 16 around drum 22. As soon as the desired number of rods to be sampled is withdrawn from conveyor 14, the drum 22 is stopped and the arms 24, 24' are pivoted back to the first position so tapes 16, 16' will not contact the articles 10.

Once the sample articles 10 have been wound in order on drum 22 they may be removed in consecutive order for testing. Any convenient means may be used to remove articles 10 from the second conveyor in order. They may be manually removed. However, it is desirable to run the tape slowly across a stripping apparatus as shown in FIGS. 5 and 6. Drum 22 is removed from the apparatus shown in FIGS. 2, 3, and 4 and mounted for rotation about an axis 40. The adhesive-coated tapes 16, 16' are threaded around idler roll 42 and into the nip of driven rolls 44 and 46. A continuous sheet of material 48 such as tissue paper is provided from roll 50 and also run into the nip of driven rolls 44 and 46 so as to be against the adhesive coating on tapes 16, 16'. Thus, tapes 16, 16' do not stick to roll 46. Stripper plate 52 shown in plan view in FIG. 6 has openings 54, 54' through which tapes 16, 16' are threaded. As tapes 16, 16' are advanced by driven rolls 44 and 46, articles are slowly stripped from tapes 16, 16' and drop in consecutive order into hopper 60.

The invention has been described in detail with particular reference to preferred embodiments thereof, but it will be understood that variations and modifications can be effected within the spirit and scope of the invention.

I claim:

1. Apparatus for intermittently sampling articles comprising
   a) a conveyor for advancing articles along a predetermined path,
   b) a supply source of adhesive-coated tape adapted to be advanced along a path adjacent to and co-directional with said articles,
   c) a drum adapted to have an end of said tape attached thereto and the tape to be wound thereon,
   d) an idler roller adapted to bear against the uncoated side of said tape and guide it between said supply source and said drum, said idler roller having a first position guiding said tape out of contact with said articles and a second position guiding said tape into contact with said articles, and
   e) means for rotating said drum in a direction and at a speed so as to advance said tape at approximately the same speed as said articles whereby when said idler roller is moved into said second position, articles are picked up by said tape and wound onto said drum.

2. Apparatus according to claim 1 which further includes means for unwinding said tape from said drum across a stripper plate to thereby remove said articles from said tape in reverse order and sequentially recover them.

3. Apparatus according to claim 1 wherein said supply source of adhesive-coated tape is a pair of spaced-apart rolls of tape.

4. Apparatus for intermittently removing, in order, fibrous rods from a conveyor on which they are being advanced at a relatively high rate of speed for the sequential testing thereof comprising
   a) a conveyor for advancing rods along a predetermined path, said rods having been deposited onto said conveyor sequentially after being cut from the end of an advancing continuous length thereof,
   b) a supply source of tape having a coating of adhesive material on one side thereof, said adhesive material having sufficient adhesiveness to pick up and support the weight of said rods, said tape adapted to be advanced along a path adjacent to and codirectional with the advancement of said rods,
   c) a drum adapted to have an end of said tape attached thereto and the tape to be wound thereon,
   d) an idler roller adapted to bear against the uncoated side of said tape and guide it between said supply source and said drum, said idler roller having a first position guiding said tape out of contact with said rods and a second position guiding said tape in contact with said rods, and
   e) means for rotating said drum in a direction and at a speed so as to advance said tape at approximately the same speed as said rods whereby when said idler roller is moved into said second position, rods are withdrawn from said conveyor by said tape and wound onto said drum in the same order as they were positioned on said conveyor.

5. Apparatus according to claim 4, which further includes means for unwinding said tape from said drum across a stripper plate to thereby remove said rods from said tape in reverse order and sequentially recover them.

6. Apparatus according to claim 4 wherein said supply source of adhesive-coated tape is a pair of spaced-apart rolls of tape.

* * * * *